(12) United States Patent
Nacher et al.

(10) Patent No.: US 6,293,111 B1
(45) Date of Patent: Sep. 25, 2001

(54) PROCESS AND APPARATUS FOR PREPARING HYPERPOLARIZED HELIUM GAS AT HIGH PRESSURE AND APPLICATION OF THE PROCESS

(75) Inventors: Jean-Pierre Nacher; Geneviève Tastevin, both of Paris; Luc Darrasse; Geneviève Guillot, both of Orsay, all of (FR)

(73) Assignee: Centre National de la Recherche Scientifique (FR)

( * ) Notice: Subject to any disclaimer, the term of this patent is extended or adjusted under 35 U.S.C. 154(b) by 0 days.

(21) Appl. No.: 09/527,666

(22) Filed: Mar. 17, 2000

Related U.S. Application Data

(63) Continuation of application No. PCT/FR98/01998, filed on Sep. 17, 1998.

(30) Foreign Application Priority Data

Sep. 17, 1997 (FR) .................................................. 97 11553

(51) Int. Cl.⁷ ....................................................... F25B 19/00
(52) U.S. Cl. ................................ 62/51.1; 62/3.1; 62/610; 62/919
(58) Field of Search ................................. 62/51.1, 55.5, 62/3.1, 610, 919

(56) References Cited

U.S. PATENT DOCUMENTS 5,642,625   7/1997   Cates, Jr. et al. ..................... 62/55.5
5,934,103 * 8/1999   Ryan et al. ............................ 62/55.5

FOREIGN PATENT DOCUMENTS

WO 95/27438   10/1995   (WO) .
WO 97/29836   8/1997    (WO) .

OTHER PUBLICATIONS

*Normal and Abnormal Pulmonary Ventilation: Visualization at Hyperpolarized He–3 MR Imaging*, Hans–Ulrich Kauczor, MD et al., Radiology, vol. 210, No. 2, pp. 564 568, Nov. 1996.

* cited by examiner

*Primary Examiner*—Ronald Capossela
(74) *Attorney, Agent, or Firm*—Schnader Harrison Segal & Lewis LLP

(57) ABSTRACT

A process for preparing hyperpolarized helium gas at high pressure including optical pumping at a resonant wavelength of about 1083 nanometers a helium gas formed by pure helium-3 isotope or by a mixture of helium-3 and helium-4 isotopes; and subjecting the helium gas to a magnetic field of about 0.01 to about 1 tesla during optical pumping and maintaining pressure higher than about 10 mbar and an apparatus for preparing a hyperpolarized helium gas at high pressure including a helium gas confinement cell; an excitation laser positioned to irradiate the helium gas; and means for generating a magnetic field of about 0.01 to about 1 tesla operatively connected to the confinement cell.

13 Claims, 3 Drawing Sheets

PROCESS AND APPARATUS FOR PREPARING HYPERPOLARIZED HELIUM GAS AT HIGH PRESSURE AND APPLICATION OF THE PROCESS

RELATED APPLICATION

This is a continuation of International Application No. PCT/FR98/01998, with an international filing date of Sep. 17, 1998, which is based on French Patent Application No. 97/11553, filed Sep. 17,1997.

FIELD OF THE INVENTION

This invention relates to the preparation of hyperpolarized helium gas at high pressure.

BACKGROUND

Hyperpolarized helium is presently used in magnetometry for the detection and measurement of weak magnetic fields. A new application of hyperpolarized helium is the in vivo exploration of the respiratory airways in humans. The principle consists of the patient inhaling a gaseous mixture containing hyperpolarized helium, followed by performing magnetic resonance imaging (MRI) to visualize the pulmonary ventilation. The imaging can be performed in a conventional strong-field tomograph (>1 tesla) or in a tomograph with a weaker field, possibly dedicated to that application. The inventors have published a report in the Académie des Sciences de Paris, Vol. 230, Series IIb, p. 671–700, 1997, describing various aspects of $^3$He gas NMR in the live lung as well as the equipment for the performance of an in vivo NMR. This type of application requires the production of hyperpolarized gas with a pressure that is sufficient to allow inhalation (P$\geq$1 bar).

Also known in the art are various processes and installations for the production of hyperpolarized helium. The general principle is based on optical laser pumping. As an example, French patent FR 8914894 describes an atomic or molecular vapor cell for optical pumping according to the prior art. The gas from this cell is constituted of a mixture of helium-3 and helium-4. However, the apparatus of the prior art only allows polarization of helium gas at low pressure, which then must be compressed at the outlet of the cell. Compression without loss of polarization of the helium gas is delicate and requires complex or expensive equipment.

The prior art also discloses two solutions for compressing the hyperpolarized helium: a mechanical compression technique using a nondepolarizing device developed by the group of Professor E. Otten of the University of Mainz and a cryogenic compression technique described in French patent FR 9601973.

FR '973 concerns an installation for the production of polarized helium-3, comprising a storage reservoir of helium-3 in liquid phase. The production of helium-3 with this type of installation requires an accumulation phase, an optical pumping phase and an evaporation phase enabling delivery of polarized helium-3.

Thus, it would be highly advantageous to resolve these drawbacks and difficulties relative to noteworthy compression by developing a process which avoids the use of sophisticated mechanical compressors and allows the production of hyperpolarized helium at high pressure with simple equipment.

SUMMARY OF THE INVENTION

The invention relates to a process for the preparation of hyperpolarized helium gas at high pressure employing an optical pumping step using a resonant wavelength close to about 1083 nanometers in a helium gas formed by pure helium-3 isotope or by a mixture of helium-3 and helium-4 isotopes, characterized in that the helium gas is subjected to a magnetic field of about 0.01 to about 1 tesla during the optical pumping step, and confined during this optical pumping step to a pressure higher than about 10 millibar (1000 pascal).

Advantageously, the helium gas is confined in a cell of generally cylindrical form presenting a transparent front surface for excitation by a laser beam, the magnetic field being created by electric coils or by a permanent magnet, antennas or electrodes producing an RF field for the creation of a plasma.

The invention also concerns a device for the preparation of hyperpolarized helium gas at high pressure comprising a helium gas confinement cell and an excitation laser, characterized in that it also comprises means for generating a magnetic field of about 0.01 to 1 tesla during the optical pumping stage.

BRIEF DESCRIPTION OF THE DRAWINGS

Better comprehension of the invention will be attained by reading the description below with reference to a nonlimitative example of implementation of a device for the production of hyperpolarized helium with reference to the attached drawings in which.

DETAILED DESCRIPTION OF THE INVENTION

Figure 1:
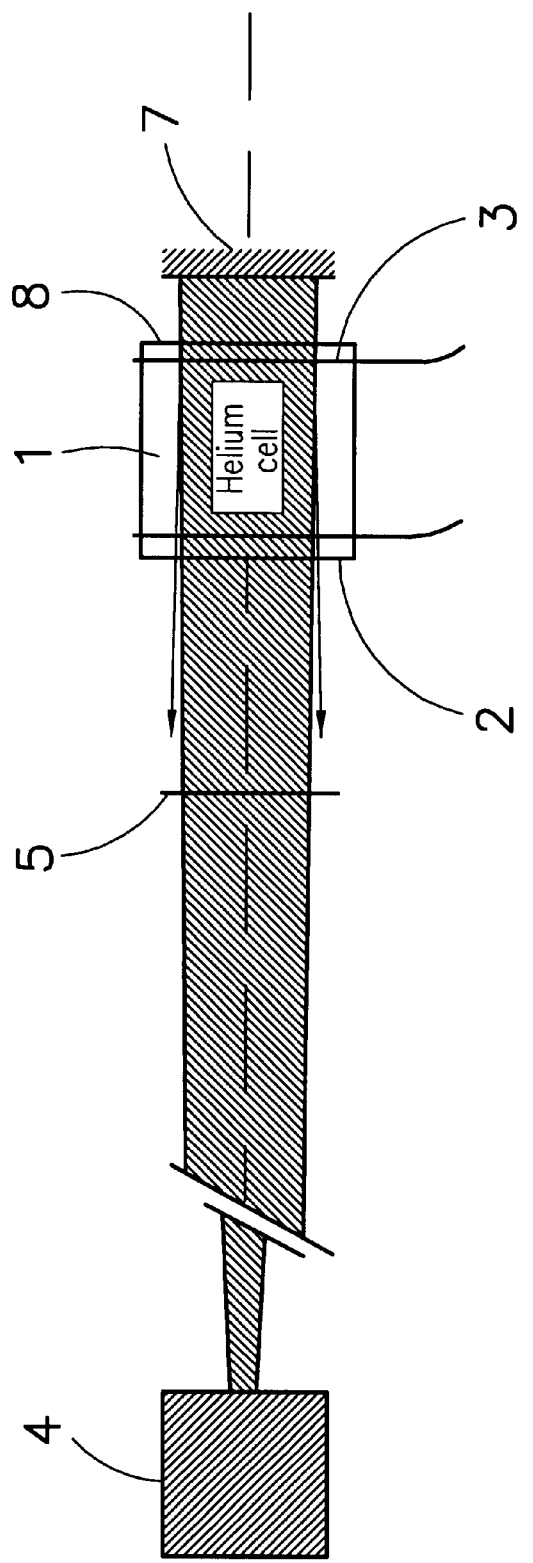
FIG. 1 shows a schematic view of an installation according to the invention.

The following description is intended to refer to specific embodiments of the invention illustrated in the drawings and is not intended to define or limit the invention, other than in the appended claims. Also, the drawings are not to scale and various dimensions and proportions are contemplated.

The installation shown in FIG. 1 comprises a cell (1) containing helium gas. It can be filled in advance, or have intake and outlet valves (22) and associated gas conducting means (24, 26) enabling introduction of helium gas at the desired pressure. Electrodes (2, 3) allow application of a radio frequency field for the formation of a plasma. A laser diode (4) with a power of 50 mW constitutes the light source. A circular polarizer (5) is interposed between the transparent front surface (6) of the cell (1) and the laser diode (4). A mirror (7) placed on the optical axis, on the side of the transparent front surface (8) of the cell (1), reflects the unabsorbed light (28) into the cell (1). This yields a noteworthy polarization in 0.1 tesla in a gas at 32 mbar, comparable to that obtained in a weak field in a gas at 4 mbar. The corresponding magnetization and thus the amplitude of the detected NMR signals are clearly greater. It was possible to produce appreciable polarizations experimentally up to pressures higher than about 130 millibar (1300 pascal).

The invention makes it possible to prepare in a helium gas a noteworthy hyperpolarization (polarization outside equilibrium can even be almost total), with the gas having a high pressure, which can possibly be as high as atmospheric pressure. The invention makes it possible to obtain a strong electronic polarization and, in addition, a strong nuclear polarization if the gas is pure helium-3 or a mixture of helium-3 and helium-4 isotopes. It includes performing optical pumping at a resonant wavelength close to about 1083 nanometers in a helium gas subjected to a static magnetic field of suitable characteristics and to an oscillating electromagnetic field enabling maintenance of a plasma suitable for optical pumping in such a static field.

The principle of optical pumping performed on the atomic transition of wavelength close to 1083 nm in a helium gas is known. In a traditional manner, a discharge is maintained to populate the triplet $2^3S_1$ metastable state, generally by a radio frequency current induced by electrodes (2, 3) external to the recipient (1) containing the gas and referred to as a cell. A weak magnetic field (generally on the order of a millitesla) is applied to maintain fixed the orientation created by optical pumping. Under these conditions the plasma only allows effective optical pumping when the pressure of the gas is on the order of a millibar (1 mbar, i.e., 100 Pa).

The polarization created by optical pumping results from the competition between the processes transferring the kinetic moment of the incident light beam to the internal variables of the atoms (polarizations of electronic and/or nuclear spin) and the relaxation processes of these polarizations towards their state of equilibrium (in which the polarization is almost zero). The effective absorption of the light beam requires, in particular, population of the metastable state of the helium atoms by the discharge with a sufficient density, but it is not possible to use an intense discharge without inducing a rapid relation.

Two processes thus contribute to limiting the density of metastable atoms while inducing relaxation of the orientation:

(1) The atomic diffusion of the atoms leads the metastable atoms to contact the walls of the cell (1) where they very rapidly deexcite by losing their orientation. In a stationary regime, this deexcitation is compensated for by the transfer (by electronic bombardment in the plasma) of atoms in the fundamental state towards a generally very excited state. A radiative cascade (in which the possible orientation of the nuclear spin prior to excitation leaves the gas in the form of polarized light) repopulates the metastable state and thereby compensates for the effects of deexcitation in contact with the walls. The weaker the pressure of the gas, the more rapid is this atomic diffusion: the coefficient of diffusion D of helium-3 is proportional to the pressure and is equivalent to 2000 cm$^2$/s at 1 mbar (their random movement diverts the atoms from their position by a distance proportional to the square root of the elapsed time, for example, 1.4 cm in 1 ms). It is known that for pressures on the order of about 0.1 mbar or lower, it is not possible in practice to produce by means of optical pumping a significant nuclear polarization in helium-3. This is primarily due to the noteworthy relaxation induced by the rapid diffusion towards the wall.

(2) The higher the absolute density of the metastable atoms, the more probable are the inelastic collisions between the metastable atoms (for example, Penning-type collisions leading to ionization). Under the influence of these collisions, two phenomena unfavorable for the optical pumping occur when the pressure increases. On the one hand, there are processes which limit in practice the density of metastable atoms at $10^{10}$ to $10^{11}$ cm$^{-3}$ in a mild discharge, with this phenomenon being largely independent of the pressure of the gas. The proportion of atoms in the metastable state is thus inversely proportional to the pressure (there are approximately $10^{17}$ atoms/cm$^3$ in a gas at 2.5 mbar and 10 times more at 25 mbar).

The indirect transfer of polarization from the light beam to the atoms in the fundamental state, which causes absorption of the light by the atoms in their metastable state, takes place more slowly as their proportion decreases, i.e., the higher the pressure, the lower the efficacy. In addition, the probability of deexcitation by such inelastic collisions becomes larger than that of deexcitation in the vicinity of the wall when the diffusion has been sufficiently slowed down by a rather high pressure. The molecular ions created by these inelastic collisions have the property of inducing a supplementary relaxation of the nuclear polarization. It is known that for pressures higher than a millbar (100 pascal), the higher the pressure the lower the efficacy of traditional optical pumping. For pressures on the order of 10 mbar (1000 pascal) or higher, slowing down the pumping and acceleration of the relaxation which result indirectly from the inelastic collisions in practice make it impossible to produce by optical pumping a significant nuclear polarization in helium-3.

Figure 3:
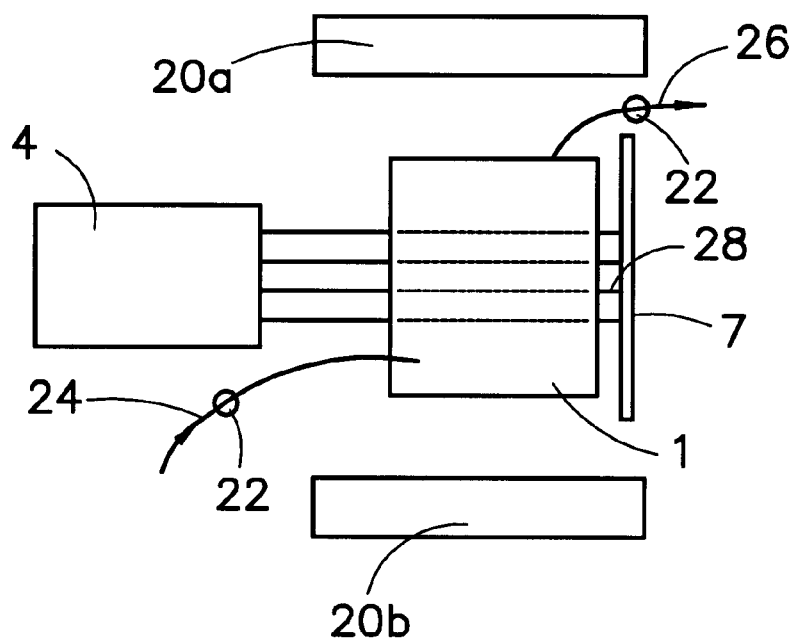
FIG. 3 shows a generalized schematic view of an apparatus according to the invention.

The invention primarily consists of applying a magnetic field of judiciously selected intensity and adapting the method for generating the plasma and the optical pumping technique (at the wavelength of 1083) to this new situation. The use of a suitable static magnetic field, generated by suitable means 20a, 20b, in FIG. 3 and described herein, (the intensity of which can be, for example, on the order of about 0.1 tesla) presents, in particular, two advantages for the optical pumping:

(1) It enables a lateral confinement of the plasma, which is a condition that makes possible maintenance of a discharge of a nature different from that obtained in a weaker field. This is with the provisio that a suitable method of excitation is adapted such that the characteristics of this plasma are more favorable to optical pumping, especially at pressures higher than about 1 mbar (at which the diffusion towards the wall is sufficiently slowed down).

(2) It enables an effective decoupling of the variables of electronic and nuclear spin in most of the excited states populated by the plasma (the Zeeman magnetic energy, which is on the order of 15 Ghz/T, exceeds the energy associated with the hyperfine coupling, which is on the order of 1 Ghz or less for these excited states). This situation has two consequences which are a priori favorable. On the one hand, during the radiative cascade mentioned above, the nuclear spin remains decoupled and conserves its polarization, the emitted light not being polarized: such an intense magnetic field thereby makes it possible to block one of the relaxation processes within the plasma. On the other hand, the structure of the atomic levels brought into play upon the radiative transition of wavelength close to 1083 nm is modified by the application of such an intense magnetic field, and the positions and probabilities of transition of these levels can be adjusted so as to enable more effective optical pumping.

The judicious use of such an intense magnetic field thus enables effective optical pumping in helium and, in particular, the creation of strong nuclear polarization in the fundamental state of helium-3, over a broad range of pressure of the gas (even for pressure higher than 10 mbar). In addition, such a field can raise the degeneration of sublevels of a quantity larger than the widening due to the Doppler effect; this makes it possible to selectively excite certain of these sublevels by using one or more optical pumping beams whose wavelength(s) are suitably selected, with large latitude in the selection of the directions and polarizations of the beams.

In addition to the conventional elements employed for the optical pumping of helium, such as are shown schematically in FIG. 1, i.e., a cell (1) containing a helium gas, a source of laser light at 1083 nm and light beam polarization means, a device for creation of a sufficiently intense magnetic field is required. This device can be a coil or a winding assembly, with passage of a direct current (resistance magnet) or a permanent magnet constituted by an assembly of elements made of a material with remanence magnetism (ferrite, for example).

The important characteristics of the field are its intensity B and its relative homogeneity. The intensity must be sufficient such that it is possible to benefit from the favorable effects: in practice a field on the order of B=100 mT is required. The homogeneity must be sufficiently good so as not to induce excessively rapid relaxation. This relaxation results from the diffusion of the atoms which means that the spatial fluctuation of the applied field induce temporal fluctuation of the field sustained by the atoms. It is known in general to calculate the resultant relaxation rate $1/T_{67\ B}$, which is proportional to $(\delta B/B^2/P)$, in which P is the pressure of the gas and $\delta B/B$ is the relative inhomogeneity of the field on the volume occupied by the gas.

In the traditional method of optical pumping of helium, a magnetic field is only required incidentally, because in practice inhomogeneous fields exist over all experience: the addition of a homogeneous field has the sole object of reducing the relative inhomogeneity on the volume of the gas and thereby the relaxing effects of the inhomogeneities resulting from the environment. The value of this field is of no importance, and it is quite possible to use the earth field, for example. In contrast, the use of an intense field is essential for the invention, and the relative inhomogeneity $\delta B/B$ is in practice determined by the geometry of the device which creates the field. A supplementary advantage of the optical pumping in a gas a thigh pressure is that the relaxation is slowed down ($T_{\delta B}$ is proportional to P) and that compact devices are sufficient for generating a field with sufficient homogeneity.

Figure 2:
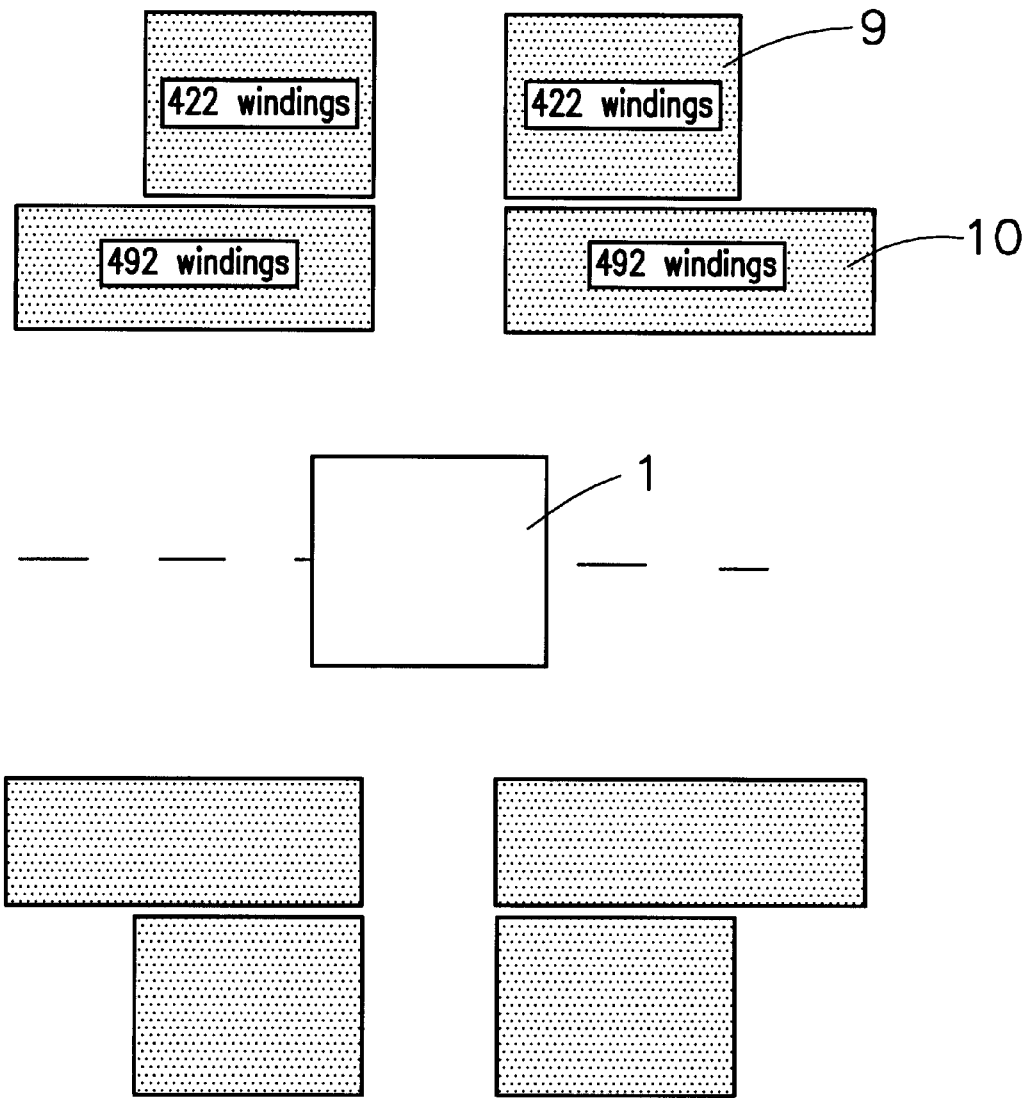
FIG. 2 shows a schematic view of the magnetic field generator which is not shown in FIG. 1.

FIG. 2 shows an example of a device for the implementation of the invention. It comprises a cell (1) placed in the core of a coil (9) (10) presenting an external diameter of 25 cm, an internal diameter of 10 cm and a length of 25 cm, the homogeneity of which on a volume of 100 cm$^3$ around its center is sufficient such that $T_{\delta B}$ is long enough that effective optical pumping can be performed when the pressure is not too low ($T_\delta$ on the order of 100 s for P=1 mbar, 100 s for 10 mbar). This field source delivers approximately 10 mT/A and dissipates 6 W/A$^2$.

A suitable magnetic field can also be produced by means of an MRI imager: either inside a weak-field imager or in the external field of an intense-field imager.

The invention resolves the problem of rapidly producing highly polarized helium directly in the form of dense gas, a result contrary to the ideas established 35 years ago regarding optical pumping at 1083 nm in helium. The invention does not present the drawbacks of the optical pumping methods described in the art, but rather combines the advantages in terms of performance. Its yield and production rate are better than those of the method using a vapor of alkaline atoms. Its high operating pressure simplifies or makes unnecessary the compression of the polarized gas generally required at the outlet of the conventional optical pumping involving metastable helium in a weak magnetic field.

According to one embodiment, the magnetic field is created at least in part by the imager. According to another embodiment, the cell is surrounded by coaxial coils to generate a magnetic field in the volume of helium gas.

Advantageously, the device according to the invention comprises a gas intake valve enabling confinement of the gas in the cell at a pressure higher than 10 millibar (1000 pascal), and an outlet valve for delivering the hyperpolarized gas after it has been polarized.

The invention also relates to an application of the process for preparation of hyperpolarized helium according to the invention for the in vivo exploration of the respiratory airways and for the NMR imaging of a body after penetration into said body of the hyperpolarized helium produced by a device according to the invention.

Although this invention has been described with reference to specific forms of apparatus and method steps, it will be apparent to one of ordinary skill in the art that various equivalents may be substituted, the sequence of steps may be varied, and certain steps may be used independently of others, all without departing from the spirit and scope of the invention defined in the appended claims.

What is claimed is:

1. A process for preparing hyperpolarized helium gas at high pressure comprising the steps of:
    confining and maintaining a helium gas at pressure of greater than about 10 mbar;
    optically pumping at a resonant wavelength of about 1083 nanometers said helium gas wherein said helium gas formed by isotopes selected from the group consisting of pure helium-3 isotope and a mixture of helium-3 and helium-4 isotopes; and
    subjecting said helium gas to a magnetic field of about 0.01 to about 1 tesla during optical pumping.

2. The process according to claim 1, wherein the helium gas is confined in a cell of substantially cylindrical shape which has a substantially transparent front surface for excitation by a laser beam and the magnetic field is created by at least one of electric coils, antennas and electrodes producing an RF field to thereby form a plasma.

3. The process according to claim 1, wherein the helium gas is confined in a cell of substantially cylindrical shape which has a substantially transparent front surface for excitation by a laser beam and the magnetic field is created by at least one of a permanent magnet, antennas, and electrodes producing an RF field to thereby form a plasma.

4. The process according to claim 1, wherein the helium gas is confined in a cell of substantially cylindrical shape which has a substantially transparent front surface for excitation by a laser beam and the magnetic field is created at least in part by an imager.

5. The process according to claim 1 further comprising the step of:
    reflecting unabsorbed light back into the confined helium gas.

6. Apparatus for preparing a hyperpolarized helium gas at high pressure comprising:
    a helium gas confinement cell having means for ingress of helium gas and means for egress of said hyperpolarized helium;
    an excitation laser positioned to irradiate helium gas within said confinement cell; and
    means for generating a magnetic field of about 0.01 to about 1 tesla operatively connected to the confinement cell;
    wherein said laser and said means for generating a magnetic field are positioned proximate said confinement cell for simultaneous effect on the helium gas contained therein.

7. The apparatus according to claim 6, further comprising one or more valves for introduction of the helium gas at a pressure higher than about 10 mbar into the confinement cell and one or more valves for the extraction of the helium gas after it has been hyperpolarized.

8. The apparatus according to claim 6, wherein the means for generating a magnetic field is a permanent magnet.

9. The apparatus according to claim 6, wherein the means for generating a magnetic field is a pair of electrodes.

10. The apparatus according to claim 6, wherein the means for generating a magnetic field is electric coils.

11. A process for in vivo exploration of respiratory airways in a patient comprising the steps of:

generating a gaseous mixture containing hyperpolarized helium obtained by optical pumping at a resonant wavelength of about 1083 nanometers a helium gas formed by pure helium-3 isotope or by a mixture of helium-3 and helium-4 isotopes;

subjecting said helium gas to a magnetic field of about 0.01 to about 1 tesla during optical pumping and maintaining pressure higher than about 10 mbar; and causing said patient to inhale a gaseous mixture containing hyperpolarized helium generated in accordance with the process defined in claim 1.

12. A process for in vivo exploration of respiratory airways in a patient comprising the steps of:

generating a gaseous mixture containing hyperpolarized helium in an apparatus comprising:

a helium gas confinement cell having means for ingress of helium gas and means for egress of said hyperpolarization helium;

an excitation laser positioned to irradiate helium gas within said confinement cell;

means for generating a magnetic field of about 0.01 to about 1 tesla operatively connected to the confinement cell;

wherein said laser and said means for generating a magnetic field are positioned proximate said confinement cell for simultaneous effect on the helium gas contained therein; and causing said patient to inhale a gaseous mixture containing hyperpolarized helium generated in accordance with the apparatus defined in claim 6.

13. The apparatus of claim 6 further comprising a mirror, placed opposite the excitation laser, for reflecting unabsorbed light back into the helium confinement cell.

* * * * *